(12) United States Patent
Ishikawa et al.

(10) Patent No.: US 8,629,900 B2
(45) Date of Patent: Jan. 14, 2014

(54) 3D ENDOSCOPE

(75) Inventors: Tomonori Ishikawa, Hino (JP);
Toshihiro Matsui, Akiruno (JP); Kenji Harano, Hachioji (JP); Natsuki Hori, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 38 days.

(21) Appl. No.: 13/343,324

(22) Filed: Jan. 4, 2012

(65) Prior Publication Data

US 2012/0162369 A1 Jun. 28, 2012

Related U.S. Application Data

(63) Continuation of application No. PCT/JP2011/061070, filed on May 13, 2011.

(30) Foreign Application Priority Data

Jul. 9, 2010 (JP) ................................. 2010-157127

(51) Int. Cl.
*H04N 13/00* (2006.01)
*H04N 13/02* (2006.01)

(52) U.S. Cl.
USPC ................... 348/45; 348/42; 348/46; 348/65

(58) Field of Classification Search
USPC ......................................... 348/42, 45, 46, 65
See application file for complete search history.

(56) References Cited

U.S. PATENT DOCUMENTS

| | | |
|---|---|---|
| 3,520,587 A | 7/1970 | Tasaki et al. |
| 5,305,098 A | 4/1994 | Matsunaka et al. |
| 5,689,365 A | 11/1997 | Takahashi |
| 2002/0035310 A1 | 3/2002 | Akui et al. |
| 2004/0190863 A1 | 9/2004 | Nishimura et al. |

FOREIGN PATENT DOCUMENTS

| | | |
|---|---|---|
| JP | 63-238842 | 10/1988 |
| JP | 1-177530 | 7/1989 |
| JP | 05-95900 | 4/1993 |
| JP | 06-261860 | 9/1994 |
| JP | 2001-242521 | 9/2001 |
| JP | 2004-141419 | 5/2004 |
| JP | 2006-235316 | 9/2006 |
| JP | 2007-532240 | 11/2007 |
| JP | 4474312 | 3/2010 |

OTHER PUBLICATIONS

English language translation of International Search Report PCT/JP2011/061070 dated Jun. 14, 2011.
European Search Report dated Jul. 6, 2012 from corresponding European Patent Application No. EP 11 803 390.1.
English Abstract of International Publication No. WO 2005/104927 A2, dated Nov. 10, 2005.
European Office Action dated Feb. 28, 2013 from corresponding European Patent Application No. EP 11 803 390.1.

*Primary Examiner* — Geepy Pe
(74) *Attorney, Agent, or Firm* — Scully, Scott, Murphy & Presser, P.C.

(57) ABSTRACT

A 3D endoscope includes an insertion portion, a left imaging unit which comprises a left imaging optical system and a left imaging device, a right imaging unit which comprises a right imaging optical system and a right imaging device, a receiving portion which receives the left imaging unit and a receiving portion which receives the right imaging unit. The 3D endoscope includes a body provided at a side of a distal end of the insertion portion, the body supporting the receiving portions at an angle to a longitudinal direction so that the inclination of a left optical axis relative to the longitudinal direction, the inclination of a right optical axis relative to the longitudinal direction, the angle of rotation of the left imaging unit around the left optical axis, and the angle of rotation of the right imaging unit around the right optical axis are adjustable.

2 Claims, 7 Drawing Sheets

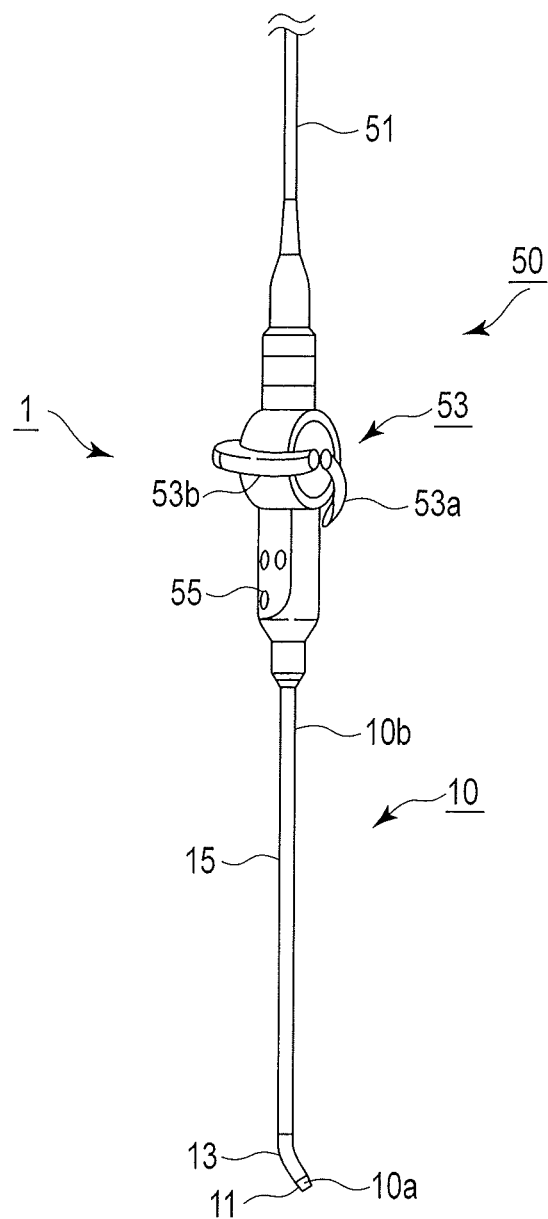
F I G. 1

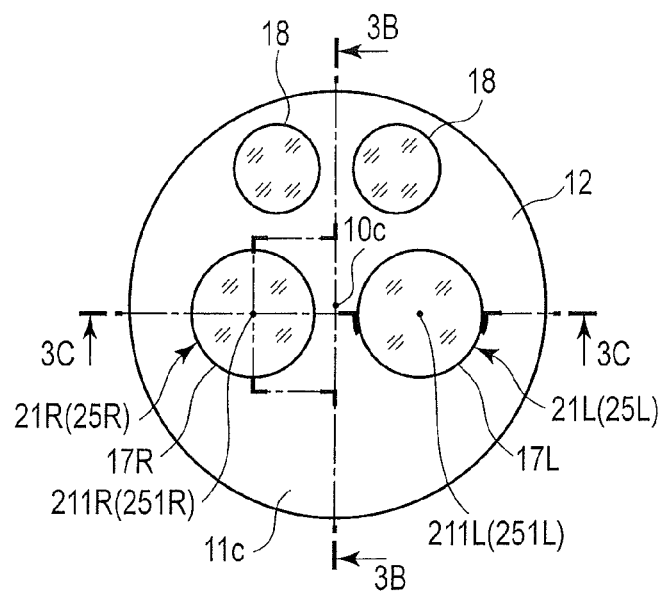
F I G. 2
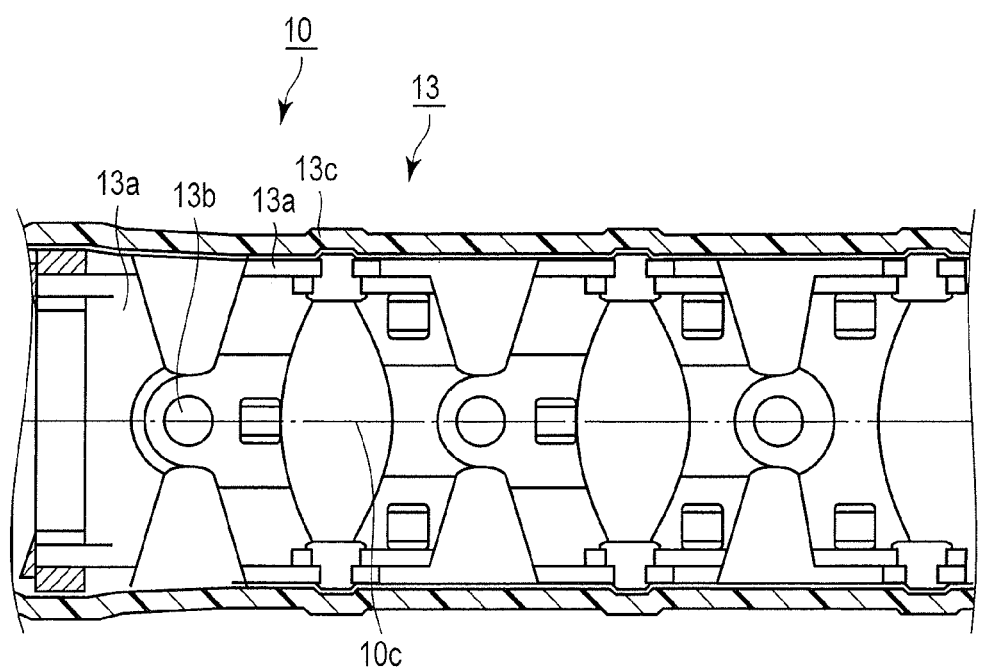
F I G. 3A

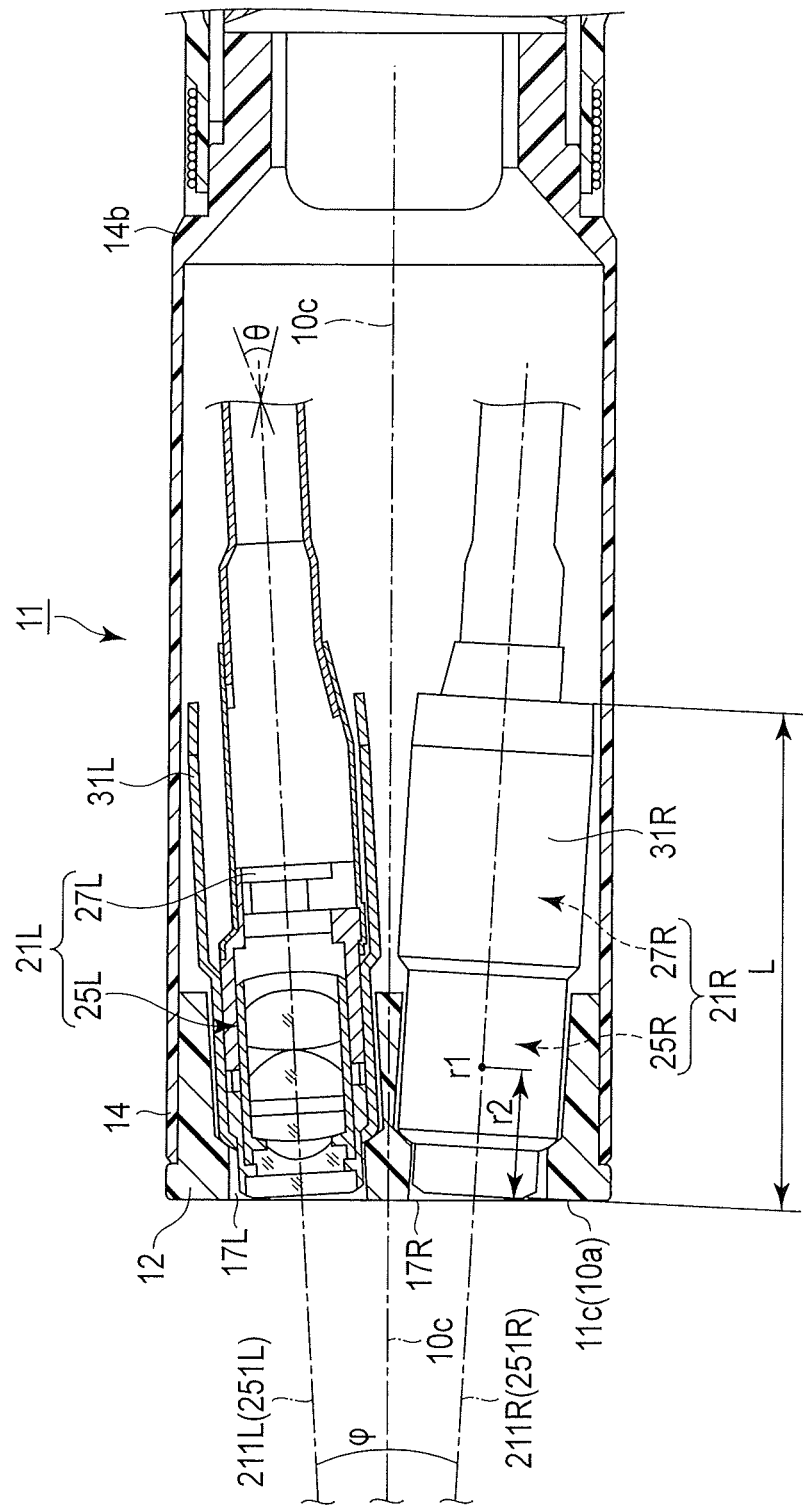
F I G. 3C

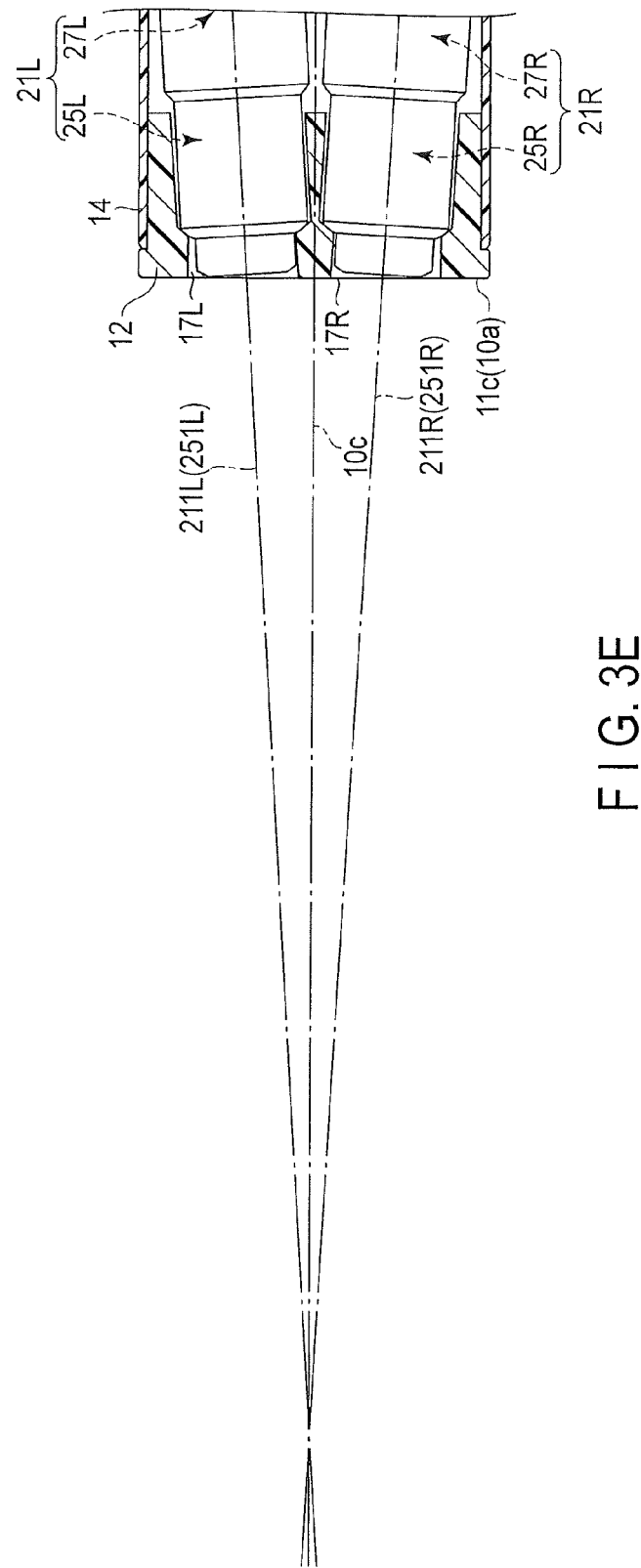
F I G. 3E

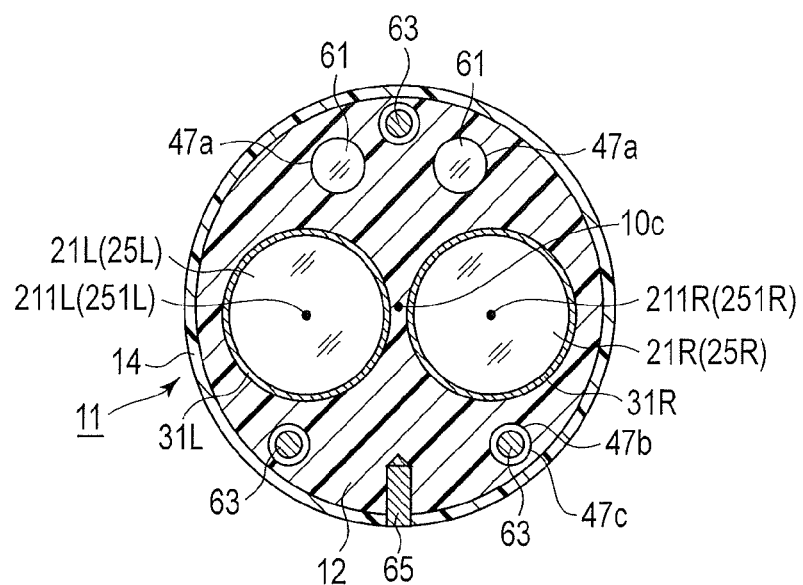
F I G. 4A
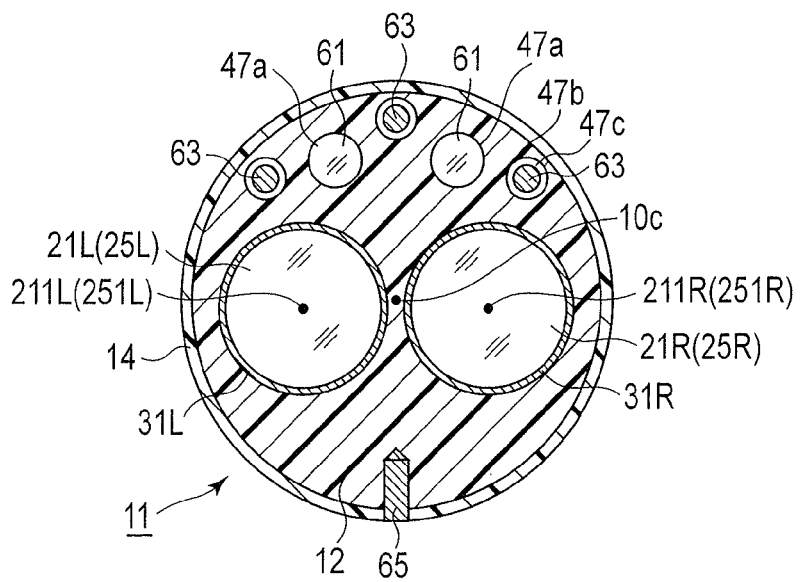
F I G. 4B

3D ENDOSCOPE

CROSS-REFERENCE TO RELATED APPLICATIONS

This application is a Continuation Application of PCT Application No. PCT/JP2011/061070, filed May 13, 2011 and based upon and claiming the benefit of priority from prior Japanese Patent Application No. 2010-157127, filed Jul. 9, 2010, the entire contents of all of which are incorporated herein by reference.

BACKGROUND OF THE INVENTION

1. Field of the Invention

The present invention relates to a 3D endoscope for three-dimensionally observing an operative site.

2. Description of the Related Art

A 3D endoscope is used to three-dimensionally observe a micro operative site, for example, in surgery within a body cavity. This 3D endoscope has a pair of right and left observation units, and a pair of right and left imaging units corresponding to the observation units. Observation optical systems of the observation units observe the operative site, and imaging optical systems of the imaging units image the operative site. Such a 3D endoscope comprises what is called a stereomicroscope capable of enlarged observation and three-dimensional observation of the operative site.

In the 3D endoscope, the central position of a left image obtained by the left imaging unit and the central position of a right image obtained by the right imaging unit need to correspond to each other at a desired point for the three-dimensional observation. Moreover, the angle of rotation of the left image around the optical axis of the left imaging optical system and the angle of rotation of the right image around the optical axis of the right imaging optical system need to correspond to each other for the three-dimensional observation. Therefore, adjustment members for adjusting the central positions and the angles of rotation are provided around the imaging units.

For example, Jpn. Pat. Appln. KOKAI Publication No. 2001-242521 has disclosed a method of adjusting the central positions and angles of rotation of a pair of right and left images by shifting or rotating an imaging device relative to imaging optical systems.

Furthermore, for example, Japanese Patent No. 4474312 has disclosed a method of providing proper three-dimensional observation by clipping out a range in which the central positions of a pair of right and left images correspond to each other at a desired point in images obtained by imaging units.

BRIEF SUMMARY OF THE INVENTION

According to an aspect of embodiments, a 3D endoscope comprising: an insertion portion to be inserted into a body cavity; a left imaging unit which comprises a left imaging optical system for a left eye and a left imaging device; a right imaging unit which comprises a right imaging optical system for a right eye and a right imaging device; a left receiving portion which receives the left imaging unit; a right receiving portion which receives the right imaging unit; and a support member provided at a side of a distal end of the insertion portion, the support member supporting the left receiving portion and the right receiving portion at an angle to the longitudinal direction of the insertion portion so that the inclination of a left optical axis of the left imaging unit relative to the longitudinal direction of the insertion portion, the inclination of a right optical axis of the right imaging unit relative to the longitudinal direction of the insertion portion, the angle of rotation of the left imaging unit around the left optical axis, and the angle of rotation of the right imaging unit around the right optical axis are adjustable, a side of a distal end of the left receiving portion and a side of a distal end of the right receiving portion have a projecting shape, and each of outer peripheral surfaces at the projecting distal ends has a spherical shape, the support member comprises a left through-hole in which the left receiving portion is disposed and a right through-hole in which the right receiving portion is disposed, the left through-hole has a spherical shape or a tapered shape so that the outer peripheral surface of the left receiving portion inclines and rotates to contact a peripheral surface of the left through-hole when the left receiving portion inclines and rotates, and the right through-hole has a spherical shape or a tapered shape so that the outer peripheral surface of the right receiving portion inclines and rotates to contact a peripheral surface of the right through-hole when the right receiving portion inclines and rotates.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a perspective view of a 3D endoscope according to an embodiment;

FIG. 2 is a front view of a distal portion of an insertion portion;

FIG. 3A is a sectional view of a curving portion;

FIG. 3C is a sectional view of the distal portion of the insertion portion along line 3C-3C shown in FIG. 2;

FIG. 3E is a diagram showing the relation between the optical axes of the imaging optical systems and a central axis 10c;

FIG. 4A is a sectional view along line 4A-4A shown in FIG. 3B; and

FIG. 4B shows a modification of the sectional view shown in FIG. 4A.

DETAILED DESCRIPTION OF THE INVENTION

Figure 3B:
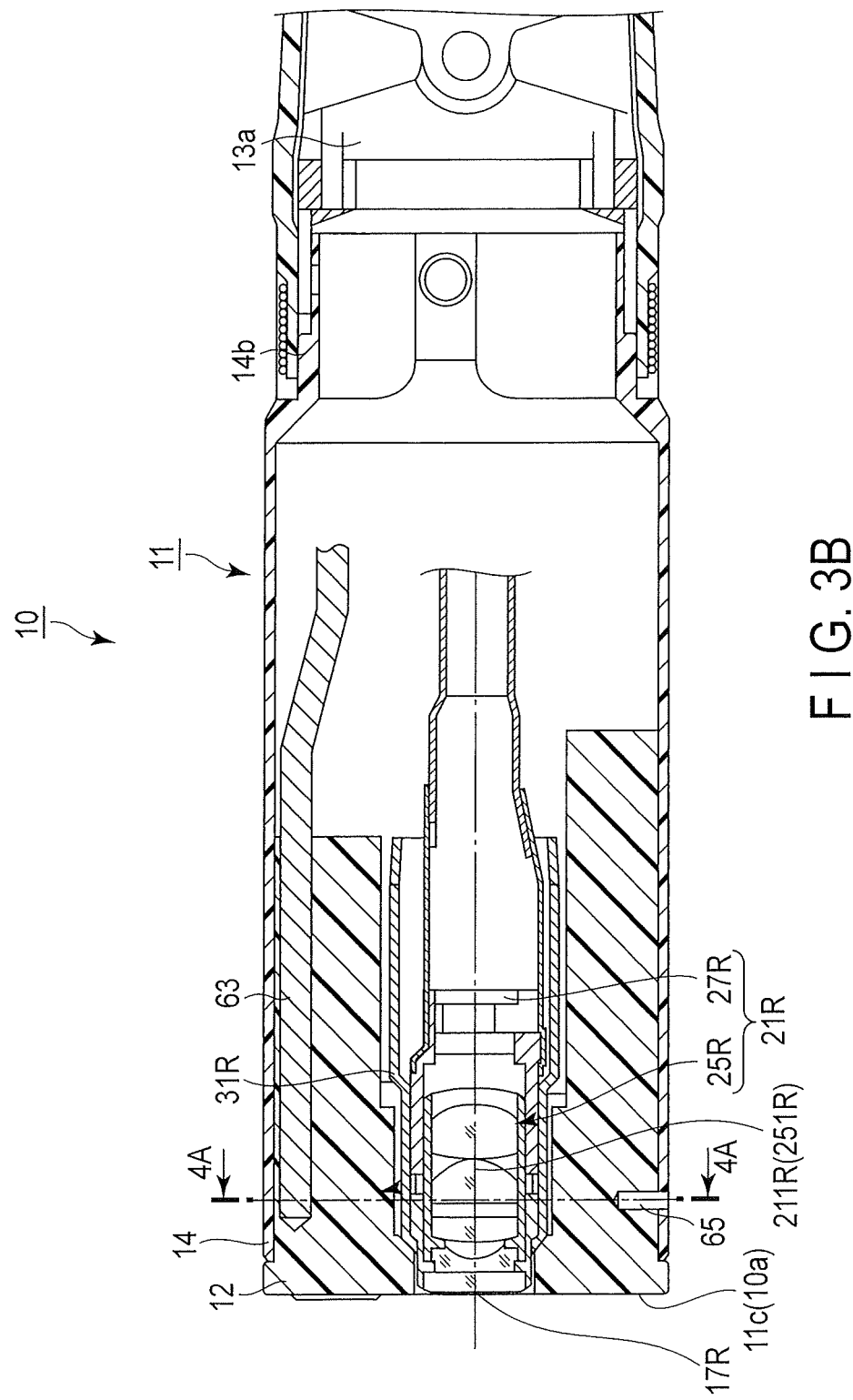
FIG. 3B is a sectional view of the distal portion of the insertion portion along line 3B-3B shown in FIG. 2.

An embodiment of the present invention will hereinafter be described in detail with reference to the drawings.

The present embodiment is described with reference to FIG. 1, FIG. 2, FIG. 3A, FIG. 3B, FIG. 3C, FIG. 3D, FIG. 3E, FIG. 4A, and FIG. 4B.

A 3D endoscope 1 according to the present embodiment shown in FIG. 1 three-dimensionally observes an operative site within a body cavity (e.g., abdominal cavity). Such a 3D endoscope 1 is, for example, a rigid endoscope applied to an abdominal procedure. This 3D endoscope 1 comprises an insertion portion 10 to be inserted into the body cavity (e.g., abdominal cavity), and an operation portion 50 which is coupled to a proximal end 10b of the insertion portion 10 and which is gripped by an operator and which performs various kinds of operations of the 3D endoscope 1.

As shown in FIG. 1, the operation portion 50 is provided with a universal cord 51. Various cables of, for example, a left imaging unit 21L, a right imaging unit 21R, and an illumination optical system 61 that will be described later are inserted through the universal cord 51. The universal cord 51 is connected to a video processor and a light source device that are not shown.

As shown in FIG. 1, the operation portion 50 is provided with a curving operation portion 53 for curving a later-described curving portion 13. The curving operation portion 53 comprises a vertical lever 53a for vertically curving the curving portion 13, and a horizontal lever 53b for horizontally curving the curving portion 13. In the operation portion 50, an unshown curving operation mechanism is provided to pull an unshown operation wires in response to the operation of the curving operation portion 53 (the vertical lever 53a and the horizontal lever 53b). The operation wires are provided in the insertion portion 10. The proximal end of the operation wires are connected to the curving operation mechanism, and the distal end of the operation wires are connected to the distal end of the curving portion 13. The curving operation portion 53 operates the operation wire so that the curving operation mechanism is driven in response to the operation of the curving operation portion 53, the operation wires are pulled by the curving operation mechanism, and the curving portion 13 remotely curves in four directions. This allows the curving portion 13 to curve toward a target site.

As shown in FIG. 1, the operation portion 50 is also provided with various operation switches 55 for operating the 3D endoscope 1 including later-described imaging devices 27L and 27R.

The insertion portion 10 is rigid, and has a length applied to an abdominal procedure. As shown in FIG. 1, the insertion portion 10 comprises a distal rigid portion 11, the curving portion 13, and a rigid portion 15, from the side of a distal end 10a of the insertion portion 10 toward the side of a proximal end 10b of the insertion portion 10. The proximal end of the distal rigid portion 11 is coupled to the distal end of the curving portion 13, and the proximal end of the curving portion 13 is coupled to the distal end of the rigid portion 15.

The rigid portion 15 is an elongated and rigid pipe. The rigid portion 15 is, for example, a rigid pipe. The proximal end of the rigid portion 15 is the proximal end of the insertion portion 10. The proximal end of the rigid portion 15 is coupled to the operation portion 50.

The curving portion 13 is connected to the above-mentioned curving operation mechanism via the above-mentioned operation wires. The operation wires are pulled by operating the curving operation portion 53. Accordingly, the curving portion 13 curves in desired directions such as vertical and horizontal directions. As the curving portion 13 curves, the position and direction of the distal rigid portion 11 change, so that the operative site is caught in observation view fields (observation windows 17L and 17R (see FIG. 2)) of later-described imaging optical systems 25L and 25R, and the operative site is illuminated with illumination light emitted from the later-described illumination optical system 61.

In addition, as shown in FIG. 3A, the curving portion 13 is constituted of joint rings 13a arranged side by side along the longitudinal axis direction of the insertion portion 10 (the insertion direction of the 3D endoscope 1). The joint rings 13a have a substantially cylindrical (annular) shape. The joint rings 13a adjacent to each other (located one after the other along a central axis 10c of the insertion portion 10) are pivotally coupled together by a pivot (support shaft) such as a rivet 13b. The joint rings 13a are thus pivotally coupled to each other such that the curving portion 13 capable of curving (pivoting) as described above is formed. Moreover, as shown in FIG. 3B, the joint ring 13a provided closest to the distal rigid portion 11 is coupled to the distal rigid portion 11.

As shown in FIG. 3A, the curving portion 13 is covered with an envelope tube 13c. This envelope tube 13c is formed, for example, by a resin material and an elastic material such as rubber. The envelope tube 13c has substantially the same shape (e.g., a hollow shape or a cylindrical shape) as the curving portion 13. The envelope tube 13c may be injection-molded by an elastic material including a (styrene-based, olefin-based, urethane-based) thermoplastic elastomer. The thermoplastic elastomer is not exclusively injection-molded, and may be molded in various ways; for example, casting, extrusion, or blowing.

As shown in FIG. 3B, the distal rigid portion 11 is, for example, cylindrically shaped, and made of a metal material. The distal rigid portion 11 comprises a body 12 and a cover 14. The distal rigid portion 11 is coupled to the joint ring 13a of the curving portion 13 at a proximal end 14b of the cover 14. As shown in FIG. 3B, the body 12 is fitted in the cover 14. As shown in FIG. 2, the observation windows 17L and 17R for the imaging optical systems 25L and 25R and an illumination window 18 for the illumination optical system 61 are provided in a distal end face 11c of the body 12. The distal end face 11c is a flat surface.

As shown in FIG. 3C, such a 3D endoscope 1 comprises the left imaging unit 21L for a left image (left eye) and the right imaging unit 21R for a right image (right eye) in order to three-dimensionally observe an operative site. The left imaging unit 21L comprises the imaging optical system 25L for the left image (left eye), and the imaging device 27L which comprises, for example, a CCD. The right imaging unit 21R comprises the imaging optical system 25R for the right image (right eye), and the imaging device 27R which comprises, for example, a CCD. Thus, the 3D endoscope 1 has two imaging optical systems and two imaging devices for right and left observations.

The imaging optical system 25L for the left image and the imaging optical system 25R for the right image have the same configuration, and the imaging device 27L for the left image and the imaging device 27R for the right image have the same configuration. Therefore, the imaging optical system 25R and the imaging device 27R are described below by way of example.

As shown in FIG. 3B and FIG. 3C, the imaging optical system 25R comprises, for example, an objective lens for observing the operative site, and an imaging lens for forming an image of the operative site observed by the objective lens.

The imaging device 27R electrically changes the image (operative site) which has passed through the objective lens and formed by the imaging lens. Various cables such as signal lines in the imaging device 27R are provided to extend to the universal cord 51 through the insertion portion 10 and the operation portion 50.

The imaging optical system 25L is provided closer to the body 12 (distal end face 11c) of the distal rigid portion 11 than the imaging device 27L, and the imaging optical system 25R is provided closer to the body 12 of the distal rigid portion 11 than the imaging device 27R.

Figure 3D:
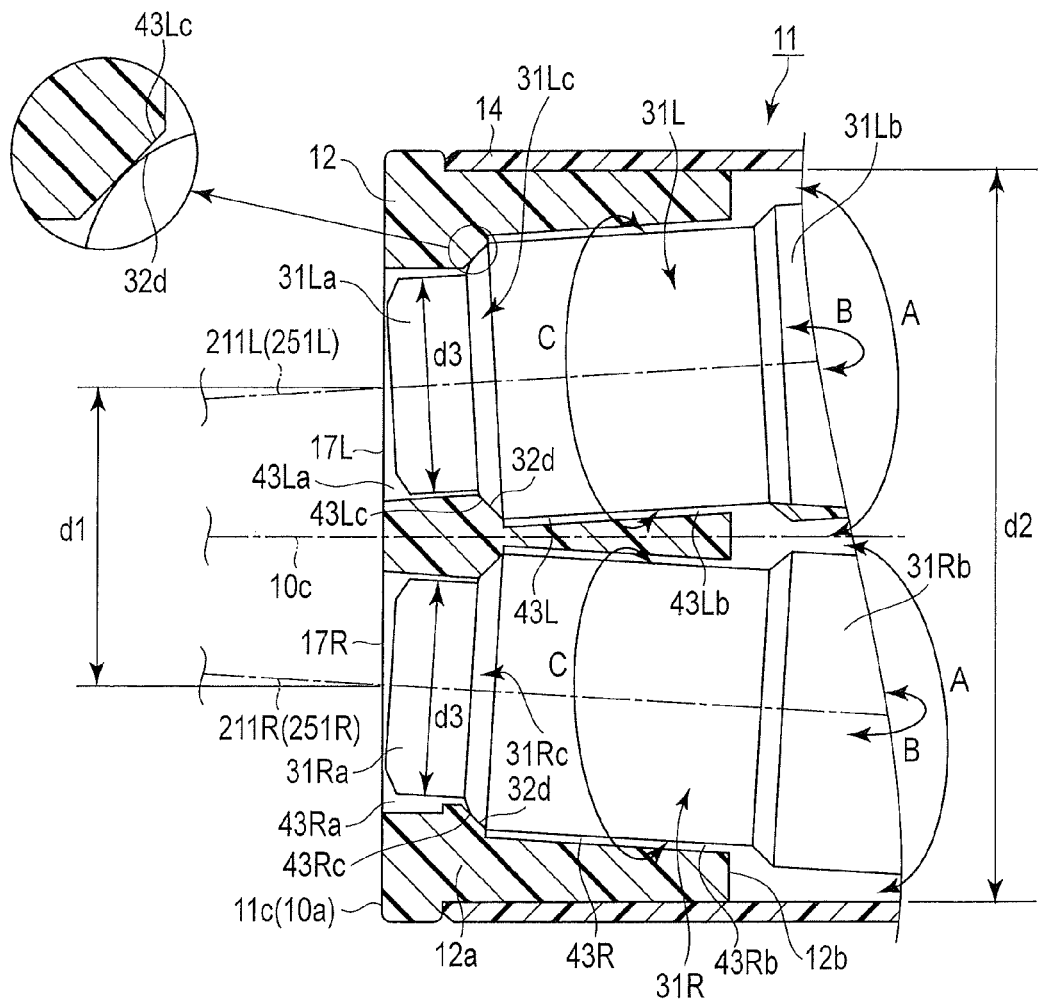
FIG. 3D is a partial enlarged view of parts around through-holes shown in FIG. 3C.

As shown in FIG. 3B, FIG. 3C, and FIG. 3D, the 3D endoscope 1 comprises a left receiving portion 31L which receives the left imaging unit 21L, and a right receiving portion 31R which receives the right imaging unit 21R. The receiving portion 31L and the receiving portion 31R are separate from each other.

The receiving portion 31L and the receiving portion 31R have the same configuration. Therefore, the receiving portion 31L is described below by way of example.

The receiving portion 31L is made of, for example, a metal, and has a stepped cylindrical shape. As shown in FIG. 3D, an outer peripheral surface 32d at a distal end 31La of the receiving portion 31L has a spherical surface 31Lc. The receiving portion 31L increases in diameter from the distal end 31La to a proximal end 31Lb of the receiving portion 31L. That is, the receiving portion 31L has a projecting shape. The distal end of the receiving portion 31R is referred to as a distal end 31Ra. The proximal end of the receiving portion 31R is referred to as a proximal end 31Rb. The spherical surface of the receiving portion 31R is referred to as a spherical surface 31Rc. The outer peripheral surface of the receiving portion 31R is referred to as the outer peripheral surface 32d.

The receiving portion 31L is provided in the distal rigid portion 11 so that the receiving portion 31L receives the imaging optical system 25L and the imaging device 27L. The receiving portion 31R is provided in the distal rigid portion 11 so that the receiving portion 31R receives the imaging optical system 25R and the imaging device 27R.

As shown in FIG. 3C and FIG. 3D, the receiving portion 31L and the receiving portion 31R are supported by the body 12 (support member) of the distal rigid portion 11 at an angle to the central axis 10c so that the inclination of a left optical axis 211L of the left imaging unit 21L relative to the central axis 10c, the inclination of a right optical axis 211R of the right imaging unit 21R relative to the central axis 10c, the angle of rotation of the left imaging unit 21L around the left optical axis 211L, and the angle of rotation of the right imaging unit 21R around the right optical axis 211R are adjustable.

The left optical axis 211L of the left imaging unit 21L represents, for example, an optical axis 251L of the imaging optical system 25L. The right optical axis 211R of the right imaging unit 21R represents, for example, an optical axis 251R of the imaging optical system 25R.

The inclinations of the above-mentioned optical axes 211L and 211R represent, for example, a position in the direction of arrow A and, for example, a position in the direction of arrow B shown in FIG. 3D. The angle of rotation of the left imaging unit 21L and the angle of rotation of the right imaging unit 21R are, for example, angles in the direction of arrow C shown in FIG. 3D.

In the present embodiment, if the optical axis 251L and the optical axis 251R do not intersect with each other at a desired position, there is misalignment between the central position of the left image and the central position of the right image. As a result, an observer cannot observe a proper three-dimensional image. For the three-dimensional observation, the optical axes 251L and 251R need to intersect with each other at a desired point which is a desired distance (e.g., 40 mm) apart from the distal end 10a (e.g., the distal end face 11c) of the insertion portion 10, as shown in FIG. 3E. Such an action is generally called center adjustment. Therefore, the receiving portions 31L and 31R need to incline in the directions of arrows A and B. Accordingly, in the 3D endoscope 1, the body 12 supports the receiving portions 31L and 31R so that the receiving portions 31L and 31R having the imaging optical systems 25L and 25R can incline relative to the central axis 10c. In other words, the body 12 supports the receiving portions 31L and 31R so that the optical axes 251L and 251R of the imaging optical systems 25L and 25R incline relative to the central axis 10c and thus the optical axes 251L and 251R intersect with each other at a desired position.

Furthermore, in the present embodiment, the observer cannot observe a proper three-dimensional image if the angle of rotation (direction) of the left image and the angle of rotation (direction) of the right image do not correspond to each other in the left image obtained by the imaging optical system 25L and the imaging device 27L and the right image obtained by the imaging optical system 25R and the imaging device 27R. For the three-dimensional observation, the angle of rotation of the left image around the optical axis 251L of the imaging optical system 25L and the angle of rotation of the right image around the optical axis 251R of the imaging optical system 25R need to correspond to each other. Such an action is generally called tilt adjustment. Therefore, the receiving portions 31L and 31R need to rotate in the direction of arrow C. Accordingly, in the 3D endoscope 1, the body 12 supports the receiving portions 31L and 31R so that the receiving portion 31L having the imaging optical system 25L and the imaging device 27L can rotate around the optical axis 251L and the receiving portion 31R having the imaging optical system 25R and the imaging device 27R can rotate around the optical axis 251R. In other words, the body 12 supports the receiving portions 31L and 31R so that the imaging optical system 25L and the imaging device 27L rotate around the optical axis 251L, the imaging optical system 25R and the imaging device 27R rotate around the optical axis 251R, and the angle of rotation of the left image and the angle of rotation of the right image correspond to each other.

As shown in FIG. 3D, the body 12 has through-holes 43L and 43R in which the receiving portions 31L and 31R are disposed. The through-holes 43L and 43R are provided at a desired distance from the central axis 10c and at an angle to the central axis 10c so that the receiving portions 31L and 31R do not contact each other during the center adjustment or the tilt adjustment. More specifically, the through-holes 43L and 43R are provided so that the distance between the center of the through-hole 43L and the center of the through-hole 43R at a proximal end 12b of the body 12 is larger than the distance between the center of the through-hole 43L and the center of the through-hole 43R at a distal end 12a of the body 12.

The through-holes 43L and 43R have the same configuration. Therefore, the through-hole 43L is described below by way of example.

As shown in FIG. 3D, the through-hole 43L has a stepped cylindrical shape. The through-hole 43L comprises a front hole 43La at the distal end 12a, a rear hole 43Lb at the proximal end 12b, and a tapered surface 43Lc intervening between the front hole 43La and the rear hole 43Lb. As shown in FIG. 3D, the front hole 43La is smaller in diameter than the rear hole 43Lb, so that the tapered surface 43Lc increases in diameter from the distal end 12a to the proximal end 12b. In addition, a front hole of the through-hole 43R is referred to as a front hole 43Ra and a rear hole of the through-hole 43R is referred to as a rear hole 43Rb. A tapered surface in the through-hole 43R is referred to as a tapered surface 43Rc.

That is, the through-hole 43L has a tapered shape so that the outer peripheral surface 32d of the receiving portion 31L inclines and rotates to contact the tapered surface 43Lc which is a part of the peripheral surface of the through-hole 43L when the receiving portion 31L inclines and rotates. The same applies to the through-hole 43R.

During the center adjustment or the tilt adjustment, the receiving portion 31L inclines and rotates so that the spherical surface 31Lc and the tapered surface 43Lc are in contact with each other. The same applies to the through-hole 43R.

The spherical surface 31Lc of the receiving portion 31L which is a step contacts the tapered surface 43Lc of the through-hole 43L which is a step. Therefore, the tapered surface 43Lc side also serves as a fall prevention portion for preventing the receiving portion 31L from falling from the through-hole 43L toward the distal end face 11c. The same applies to the through-hole 43R.

In such circumstances, the inclinations and rotations of the receiving portions 31L and 31R are adjusted by unshown adjustment members such as screws. Following such adjustment, the receiving portions 31L and 31R are adhesively fixed to the body 12, for example, by an unshown adhesive agent that fills the through-holes 43L and 43R.

Furthermore, in the configuration described above, the rotation central position of the imaging optical systems 25L and 25R is r1 when the receiving portions 31L and 31R rotate in the directions of arrows A and B, as shown in FIG. 3C.

As shown in FIG. 3C, the distance from the distal ends of the imaging optical systems 25L and 25R to r1 along the optical axes 251L and 251R is r2.

As shown in FIG. 3C, the total length of the receiving portions 31L and 31R is L.

As shown in FIG. 3C, the center adjustment allowance for the inclinations of the optical axes 251L and 251R in the imaging units 21L and 21R is θ.

As shown in FIG. 3C, the angle (inward angle) of the optical axes 251L and 251R of the imaging units 21L and 21R is φ.

As shown in FIG. 3D, the distance between the optical axes 251L and 251R of the imaging optical systems 25L and 25R in the distal end face 11c is d1.

As shown in FIG. 3D, the inside diameter of the distal rigid portion 11 of the 3D endoscope 1 is d2.

As shown in FIG. 3D, the outside diameter of the imaging optical systems 25L and 25R is d3.

In this case, r2 needs to satisfy Equation (1) using L, θ, φ, d1, d2, and d3.

$$(d1+d3-d2+(2\theta+\phi)L)/2\theta \leq r2 \leq (d1-d3)/2\theta \quad (1)$$

This can eliminate the problem where the receiving portions 31L and 31R cannot be received in the 3D endoscope 1, for example, after the adjustment of the angles of the imaging units 21L and 21R.

As shown in FIG. 4A and FIG. 4B, the body 12 also supports the illumination optical system 61 for illuminating the operative site with illumination light, and a heat release member 63 for releasing, toward the proximal end 10b of the insertion portion 10, heat generated at the distal end 10a of the insertion portion 10 (more specifically, the imaging units 21L and 21R).

As shown in FIG. 4A, the body 12 has an illumination opening 47a for supporting the illumination optical system 61, and a heat release opening 47b for supporting the heat release member 63. The illumination optical system 61 is fixed to the illumination opening 47a, for example, by an unshown adhesive agent that fills the illumination opening 47a, or is fitted into the illumination opening 47a. The heat release opening 47b has an outer peripheral opening 47c which is open toward an outer peripheral surface 12c of the body 12. The heat release member 63 is disposed in the heat release opening 47b, and is fixed to the body 12, for example, by unshown solder disposed in the outer peripheral opening 47c. At least one heat release member 63 and at least one heat release opening 47b have only to be provided around the illumination optical system 61 and the imaging units 21L and 21R. As shown in FIG. 4B, the heat release member 63 and the heat release opening 47b may be provided, for example, along the outer peripheral surface 12c of the body 12 in the vicinity of the illumination optical system 61. The heat release member 63 and the heat release opening 47b may be provided at an equal distance around the optical axis of the insertion portion 10.

Various cables such as the signal lines in the illumination optical system 61 are provided to extend to the universal cord 51 through the insertion portion 10 and the operation portion 50. The distal end of the illumination optical system 61 faces the illumination window 18. The heat release member 63 is provided to extend to the operation portion 50 through the insertion portion 10.

The body 12 is disposed in the side (distal rigid portion 11) of the distal end 10a of the insertion portion 10 to support the receiving portions 31L and 31R, the illumination optical system 61, and the heat release member 63. As shown in FIG. 3B, the body 12 is fixed to the cover 14, for example, by a fixing member 65 such as a screw.

Now, the center adjustment and the tilt adjustment in the left imaging unit 21L and the right imaging unit 21R according to the present embodiment are described. The method of adjustment in the left imaging unit 21L is the same as the method of adjustment in the right imaging unit 21R. Therefore, the method of adjustment in the left imaging unit 21L is described by way of example.

The receiving portion 31L receives, for example, the imaging optical system 25L and the imaging device 27L. The receiving portion 31L is disposed in the through-hole 43L provided at an angle to the longitudinal direction of the insertion portion 10. Thus, the receiving portion 31L is supported by the body 12 in a temporarily inclined state. At the same time, the spherical surface 31Lc of the receiving portion 31L contacts the tapered surface 43Lc of the through-hole 43L. The tapered surface 43Lc prevents the receiving portion 31L from falling from the through-hole 43L toward the distal end face 11c.

The receiving portions 31L and 31R are inclined relative to the central axis 10c by the unshown adjustment members so that the optical axis 251L and the optical axis 251R intersect with each other at a desired point which is at a desired distance from the distal end 10a (e.g., the distal end face 11c) of the insertion portion 10, as shown in FIG. 3E, for the center adjustment in a condition in which the spherical surface 31Lc and the tapered surface 43Lc are in contact with each other. That is, the receiving portions 31L and 31R incline in the directions of arrows A and B. At the same time, the spherical surface 31Lc and the tapered surface 43Lc contact each other, and the spherical surface 31Lc slides on the tapered surface 43Lc in the directions of arrows A and B, as shown in FIG. 3D. Also, the spherical surface 31Rc and the tapered surface 43Rc contacts each other, and the spherical surface 31Rc slides on the tapered surface 43Rc in the directions of arrows A and B, as shown in FIG. 3D.

At the same time, the through-holes 43L and 43R are at an angle to the central axis 10c. This ensures that the inclined optical axes 251L and 251R intersect with each other without being blocked by the body 12.

As a result, the central position of the left image and the central position of the right image correspond to each other.

Moreover, the receiving portions 31L and 31R are rotated around the optical axes 251L and 251R by the unshown adjustment members for the tilt adjustment in a condition in which the spherical surface 31Lc and the tapered surface 43Lc are in contact with each other. At the same time, the receiving portions 31L and 31R rotate around the optical axes 251L and 251R so that the angle of rotation of the left image around the optical axis 251L of the imaging optical system 25L and the angle of rotation of the right image around the optical axis 251R of the imaging optical system 25R correspond to each other. That is, the receiving portions 31L and 31R rotate in the direction of arrow C, as shown in FIG. 3D. At the same time, the spherical surface 31Lc and the tapered surface 43Lc contact each other, and the spherical surface 31Lc slides on the tapered surface 43Lc in the direction of arrow C, as shown in FIG. 3D. Also, the spherical surface 31Rc and the tapered surface 43Rc contacts each other, and the spherical surface 31Rc slides on the tapered surface 43Rc in the direction of arrow C, as shown in FIG. 3D.

The body 12 is a support member which supports the receiving portions 31L and 31R so that the above-described inclination and rotation are adjustable. The through-holes 43L and 43R are then filled with the adhesive agent. More specifically, the clearance between the receiving portions 31L and 31R in the through-holes 43L and 43R and the body 12 is filled with the adhesive agent. As a result, the receiving portions 31L and 31R are adhesively fixed to the body 12.

In such a condition, the illumination optical system 61 illuminates the operative site with illumination light, the left imaging unit 21L and the right imaging unit 21R image the operative site, and the operative site is displayed by an unshown display unit.

At the same time, the illumination optical system 61, the left imaging unit 21L, and the right imaging unit 21R generate heat. This heat is transmitted to the heat release member 63 via the body 12. The heat release member 63 releases this heat to the proximal end 10b of the insertion portion 10. As a result, the distal end 10a (distal rigid portion 11) is cooled off.

Thus, in the present embodiment, the center adjustment can be made by the receiving portions 31L and 31R and the body 12, so that the central position of the left image and the central position of the right image can correspond to each other, and the acquisition of an improper three-dimensional image can be prevented. Moreover, in the present embodiment, the tilt adjustment can be made by the receiving portions 31L and 31R and the body 12, so that the angle of rotation of the right image and the angle of rotation of the left image can correspond to each other, and the right and left images can correspond to each other. Further, in the present embodiment, the center adjustment and the tilt adjustment are made by rotating and inclining the receiving portions 31L and 31R relative to the body 12 which supports the receiving portions 31L and 31R, the illumination optical system 61, and the heat release member 63 instead of providing the adjustment members in the distal rigid portion 11. Thus, in the present embodiment, the distal rigid portion 11 can have a small diameter. Moreover, in the present embodiment, as it is not necessary to clip out an image, image deterioration can be prevented.

Furthermore, in the present embodiment, the distal ends 31La and 31Ra have the spherical surfaces 31Lc and 31Rc, and the through-holes 43L and 43R have the tapered surfaces 43Lc and 43Rc, such that the receiving portions 31L and 31R can be easily and smoothly rotated and inclined relative to the body 12.

It should be understood that the arrangement of the spherical surfaces 31Lc and 31Rc and the tapered surfaces 43Lc and 43Rc may be reversed. That is, functions and advantageous effects similar to those according to the present embodiment are provided if tapered surfaces are formed on the side of the spherical surfaces 31Lc and 31Rc and spherical surfaces are formed on the side of the tapered surfaces 43Lc and 43Rc. It should also be understood that spherical surfaces may be arranged instead of the tapered surfaces 43Lc and 43Rc so that the spherical surfaces contact each other.

Moreover, in the present embodiment, the through-holes 43L and 43R are provided at an angle and at a desired distance from the central axis 10c. Therefore, in the present embodiment, the distance between the center of the through-hole 43L and the center of the through-hole 43R at the proximal end 12b is, larger than the distance between the center of the through-hole 43L and the center of the through-hole 43R at the distal end 12a. Consequently, in the present embodiment, it is possible to prevent the receiving portions 31L and 31R from contacting each other even if inclined or rotated as described above. Further, in the present embodiment, the through-holes 43L and 43R are inclined as described above, so that it is possible to prevent the inclined optical axes 251L and 251R from being blocked by the body 12, and ensure that the optical axes 251L and 251R intersect with each other at a desired point.

Still further, in the present embodiment, the spherical surfaces 31Lc and 31Rc contact the tapered surfaces 43Lc and 43Rc, so that it is possible to prevent the receiving portions 31L and 31R from falling from the through-holes 43L and 43R toward the distal end face 11c.

Yet further, in the present embodiment, heat generated from the illumination optical system 61, the left imaging unit 21L, and the right imaging unit 21R can be released toward the proximal end 10b of the insertion portion 10 by the heat release member 63. As a result, the distal end 10a can be cooled off.

The present invention is not completely limited to the embodiment described above, and modifications of components can be made at the stage of carrying out the invention without departing from the spirit thereof. Further, various inventions can be made by properly combining the components disclosed in the embodiment described above.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A 3D endoscope comprising:
   an insertion portion to be inserted into a body cavity;
   a left imaging unit which comprises a left imaging optical system for a left eye and a left imaging device;
   a right imaging unit which comprises a right imaging optical system for a right eye and a right imaging device;
   a left receiving portion which receives the left imaging unit;
   a right receiving portion which receives the right imaging unit; and
   a support member provided at a side of a distal end of the insertion portion, the support member supporting the left receiving portion and the right receiving portion at an angle to a longitudinal direction of the insertion portion so that the inclination of a left optical axis of the left imaging unit relative to the longitudinal direction of the insertion portion, the inclination of a right optical axis of the right imaging unit relative to the longitudinal direction of the insertion portion, the angle of rotation of the left imaging unit around the left optical axis, and the angle of rotation of the right imaging unit around the right optical axis are adjustable,
   wherein a side of a distal end of the left receiving portion and a side of a distal end of the right receiving portion have a projecting shape, and each of outer peripheral surfaces at the projecting distal ends has a spherical shape, the support member comprises a left through-hole in which the left receiving portion is disposed and a right through-hole in which the right receiving portion is disposed, the left through-hole has a spherical shape or a tapered shape so that the outer peripheral surface of the left receiving portion inclines and rotates to contact a peripheral surface of the left through-hole when the left receiving portion inclines and rotates, and the right through-hole has a spherical shape or a tapered shape so that the outer peripheral surface of the right receiving portion inclines and rotates to contact a peripheral surface of the right through-hole when the right receiving portion inclines and rotates.

2. A 3D endoscope according to claim 1, wherein the left through-hole and the right through-hole are provided at a desired distance from a central axis of the insertion portion and at an angle to the central axis, and wherein the left through-hole and the right through-hole are provided so that the distance between a center of the left through-hole and the center of the right through-hole at a proximal end of the support member is larger than a distance between the center of the left through-hole and the center of the right through-hole at a distal end of the support member.

* * * * *